United States Patent [19]

Dullien

[11] Patent Number: 5,480,776
[45] Date of Patent: Jan. 2, 1996

[54] METHOD FOR PREDICTION OF PREMATURE LABOR

[75] Inventor: Vivian K. Dullien, Boulder, Colo.

[73] Assignee: Biex, Inc., Boulder, Colo.

[21] Appl. No.: 242,034

[22] Filed: May 12, 1994

Related U.S. Application Data

[63] Continuation of Ser. No. 952,438, Sep. 28, 1992.

[51] Int. Cl.$^6$ .......................... G01N 33/74; G01N 33/53
[52] U.S. Cl. .......................... 435/7.9; 435/7.93; 436/510; 436/65; 436/127; 436/131
[58] Field of Search .................................. 435/7.9, 7.93; 436/65, 510, 814, 127, 131, 164

[56] References Cited

U.S. PATENT DOCUMENTS

| | | | |
|---|---|---|---|
| 4,454,232 | 6/1984 | Breglio et al. | 436/504 |
| 5,028,535 | 7/1991 | Buechler et al. | 435/7.93 |

OTHER PUBLICATIONS

Nobuaki Furuhashi, Yoshinobu Tachibana, Osamu Shinkawa, Tomomi Takahashi, Mikio Tanaka, Masunori Hiruta, Masakuni Suzuki: Retrograde Time-Scale Analysis of Human Placental Lactogen, Beta Human Chorionic Gonadotropin, and Unconjugated Estriol Levels in Human Maternal Serum from the Onset of Spontaneous Labor (1984) Gynecol. obstet. Invest. 18: 264–268.
Toshiaki Suzuki, Kumiko Hirato, Koichi Ogawa, Takumi Yanaihara and Tetsuya Nakayama: Changes in Steroids in Amniotic Fluid in Relation to the Initiation of Labor (1984) Acta Obst. Gynaec. Jpn. 36: 1841–1850.
Takumi Yanaihara, Etsuo Fukushima, Toshio Kosaki, Motomi Kanazawa, Kazuyuki Suzuki and Tetsuya Nakayama: "Hormonal Changes in Relation to the Parturition" Int. Congr. Ser.—Excerpta Med. (1983) 598:434–438.
Leon Speroff, Robert H. Glass and Nathan G. Kase: In Clinical Gynecologic Endocrinology and Infertility (1989) Williams & Wilkins Fourth Edition pp. 321–326 and 344–350.
Denise M. Main in Diseases of the Newborn, Eds: H. William Taeusch, Roberta A. Ballard, and Mary Ellen Avery: (1991) W. B. Saunders Company pp. 87–92.
Jay D. Iams, Rebecca Stilson, Frances F. Johnson, Ruth A. Williams, and Robert Rice: (1990) Am. J. Obstet. Gynecol. 162:486–490.
Michael Katz, Karen Goodyear, and Robert K. Creasy: Early signs and symptoms of preterm labor (1990) Am. J. Obstet. Gynecol. 162:1150–3.
C. M. Salafia, C. A. Vogel, A. M. Vintzileos, K. F. Bantham, J. Pezzullo, and L. Silberman: Placental pathologic findings in preterm birth (1991) Am. J. Obstet. Gynecol. 165:934–8.
Alfredo M. Germain, Guillermo J. Valenzuela, Milenko Ivankovic, Charles A. Ducsay, Cristian Gabella, and Maria Seron-Ferre: Relationship of circadian rhythms of uterine activity with term and preterm delivery (1993) Am. J. Obstet. Gynecol. 168:1271–7.
Roberto Romero: Basic Mechanisms in Term and Preterm Labor (1993) SPO Postgraduate Course.
H. Frank Andersen and Irwin R. Merkatz: In Obstetrics and Gynecology (1990) J. B. Lippincott Company Sixth Edition pp. 335–351.
Wiggo Fischer-Rasmussen, Martin Vahl Gabrielsen and Tove Wisborg: Relation of Estriol in Saliva to Serum Estriol During Normal Pregnancy (1981) Acta Obstet. Gynecol. Scand. 60:417–420.
J. J. Evans, A. R. Wilkinson and D. R. Aickin: Salivary Estriol Concentrations during Normal Pregnancies, and a Comparison with Plasma Estriol (1984) Clin. Chem. 30/1, 120–121.
Furuhashi et al. Chem. Abst. vol. 102 (1985) p. 106,522M.
Suzuki et al.—Chem. Abst. vol. 101 (1984) p. 222,937d.
Yanaihara et al.—Chem. Abst. vol. (1983) p. 133,948f.
Darne et al., 1987, Increased saliva oestriol to progesterone ratio before idiopathic preterm delivery: a possible predictor for preterm labour Brit Med J 294:270–72.
Lagerström et al., 1990, Maternal serum levels of estriol, prolactin human placental lactogen and chorionic genedotal related to fetal sex in normal and abnormal pregnancies Gynecol Obstet Invest 30:198–203.

Primary Examiner—Toni R. Scheiner
Assistant Examiner—James L. Grun
Attorney, Agent, or Firm—Cooley Godward Castro Huddleson & Tatum

[57] ABSTRACT

A method for detecting the onset of labor in a patient, which comprises analyzing a body fluid of the patient for estriol concentration; correlating the concentration with a standard value; and relating a higher concentration of estriol relative to the standard value as an indication of potential onset of pre-term labor. The standard is usually selected from the group consisting of (1) a predetermined range of estriol concentrations for the body fluid in normal pregnant humans at a preselected time relative to normal, full-term delivery, or (2) a previously measured estriol concentration of the same body fluid of the same pregnant human. Use of this method does not require determination of an estriol/progesterone concentration ratio in the body fluid being test.

9 Claims, No Drawings

METHOD FOR PREDICTION OF PREMATURE LABOR

CROSS REFERENCE TO RELATED APPLICATIONS

This application is a continuation of U.S. application Ser. No. 07/952,438, filed Sep. 28, 1992.

INTRODUCTION

1. Technical Field

This invention is related to methods for detection of termination of pregnancy by premature labor and is particularly directed to assays that predict onset of labor by detection of hormone levels.

2. Background

Estrogens, which are 18-carbon steroids with an aromatic A ring, a phenolic hydroxyl group at position 3 of the A ring, and an oxygen functional group (either hydroxyl or carbonyl) at position 17 of the D ring, produce a wide variety of effects on specific target organs and on the body as a whole, working either alone or in conjunction with other hormones. Most studies of estrogens have focused on estradiol (sometimes referred to as $E_2$, which refers to the presence of two hydroxyl groups), which has been considered to be the principal active estrogen. However, estradiol is not a useful indicator of onset of labor in pregnant humans, as discussed in Block et al., *Am. J. Obstet. Gynecol.* 150:716–22 (1984), which flatly states that pre-term delivery is not predicted by serial plasma estradiol (or progesterone) concentration measurements.

Estriol ($E_3$) was initially considered to be an oxidative degradation product of estradiol metabolism, although studies have now indicated the existence of biological effects associated with estriol that are not associated with estradiol. For example, estriol production in pregnant women is now known to be associated with the placenta (at least in part). However, the presence of extraneous estriol resulting from estradiol metabolism has hindered the use of estriol as a measure of hormonal activity. On the other hand, the increased solubility in body fluids of estriol relative to estradiol and its resulting appearance in unconjugated form in a variety of body fluids makes estriol a desirable target for analysis, once a thorough understanding of its association with biological activity can be achieved.

The relationship of estriol in saliva to serum estriol during normal pregnancy was studied by Fischer-Rasmussen et al., *Acta Obst. Gynecol. Scand.* 60:417–420 (1981). In another study, salivary estriol and progesterone concentrations were measured to determine whether a fall in progesterone level or an increase in the estrogen:progesterone ratio changed in women before the onset of the first stage of labor. See Lewis et al., *J. Endocr.*, 115:177–181 (1987). This study concluded that neither hormone decreased in concentration before the onset of the first stage of labor, and the ratio of estriol to progesterone was unchanged for the last two weeks of pregnancy, providing no evidence to support the claims by others that parturition in women is preceded by a significant fall in the concentration of progesterone. Evans et al., *Clinical Chemistry*, 30:120–121, describes salivary estriol concentrations during normal pregnancies and a comparison with plasma estriol. Measurement of plasma estriol during pregnancy is described as widely used for monitoring fetal well-being, and the study was conducted to determine whether salivary and plasma estriol concentrations could be used to replace previously obtained urinary estriol measurements for this purpose. However, there are no proposals to relate estriol concentrations to clinical situations other than fetal well-being. Dame et al., *British Medical Journal*, 294:270–272 (1987), proposes that an increased salivary estriol to progesterone ratio might be a possible predictor for pre-term labor. However, the complex interaction of these two hormones prevents utilization of this measurement in a simple assay.

Accordingly, it is an object of this invention to develop a thorough understanding of the relationship of estriol concentrations in various body fluids to underlying biological functions and to use diagnostic assays for estriol to evaluate the existing and/or potential biological state of the patient from whom the estriol sample has been obtained.

SUMMARY OF THE INVENTION

The present invention provides a method for detecting the onset of labor, especially pre-term labor, in a pregnant human, which comprises analyzing a body fluid of the pregnant human for estriol concentration; correlating the concentration with a standard value selected from the group consisting of (1) a predetermined range of estriol concentrations for the body fluid in normal pregnant humans or (2) a previously measured estriol concentration of the body fluid of the pregnant human; and relating a higher concentration of estriol relative to the standard value as an indication of potential onset of pre-term labor. Use of this method does not require determination of an estriol/progesterone concentration ratio in the body fluid being tested which was previously thought to be necessary for using estriol concentrations to evaluate biological conditions.

DESCRIPTION OF SPECIFIC EMBODIMENTS

The present invention provides a method for detecting the onset of labor, especially pre-term labor, in a pregnant human by simply measuring a body fluid for estriol concentration, This method is simpler than prior techniques and provides an assay that can be carried out by a patient at home, obviating the necessity of providing samples to a professional laboratory at a location distant from the patient and the resulting delay, For example, the assay can be carried out on a single saliva sample using a simple diagnostic kit with an enzyme label, Similar assays for other substances are now available, and a laboratory assay for estriol using radioactive labels is available commercially.

In this invention, there are no limitations on the type of assay used to measure estriol. Any of the current assays for estriol can be used, as well as assays that may be developed in the future. Examples of estriol assays are described in detail below.

The assay can be carried out on any sample of body fluid, such as blood (or a blood fraction, especially serum or plasma), urine, cervical or vaginal secretions, sweat, or saliva. Estriol is sufficiently soluble in water so that it is distributed in fluids throughout the body. Saliva is preferred for simplicity of sampling and because, unlike in urine, detection is not complicated by the presence of estrogen conjugates.

A "sample" is the material being analyzed and is usually of direct biological origin, although pre-treatment may have removed some of the normal biological compounds normally associate with the analyte (such as red cells separated from plasma in a whole blood sample). Assays are preferably directed to detection to free estriol, since conjugated estriol has reduced biological activity. In saliva about 92% of estriol is in the free form, while most estriol in urine is present as a conjugate. As will be clear to those familiar with steroid metabolism, an estriol conjugate is a compound formed by formation of a covalent linkage of a non-steroidal compound to estriol. Linkage is typically through a hydroxyl group of the steroidal ring system. The non-steroidal component can be inorganic (e.g., a sulfate group) or organic (e.g., a glucuronide group).

In the broader aspects of the invention, there are no limitations on the collection and handling of samples as long as consistency is maintained. With some body fluids, such as saliva and plasma, there is little diurnal variation in estriol levels. For other fluids, notably urine, variations occur, and it is preferred to eliminate variations to the extent possible, for example by taking samples at the same time of day. However, other techniques can be utilized to ensure consistency of measurement of analytes in clinical fluids. For example, creatinine can be measured concurrently with estriol in urine. Creatinine is produced at a constant rate in the kidneys, and measurement of creatinine concentration allows correction of volume errors in urine samples, as is well known in the art.

If desired (but not required in the broadest applications of this invention), and depending on the source of the fluid being tested, free estriol can be separated from estriol conjugates. Techniques for such separations are known in the art. See, for example, Evan, *N.Z. Med. Lab. Tech.* 33:86 (1979), which describes such separations as well as two radioimmunoassays useful for measuring plasma estriol. However, these separations are generally difficult, and assays that do not require separation, either because of the use of specific antibodies or other binding compounds that differentiate between free and conjugated estriol, or because the sample is obtained from a source containing mostly free estriol, such as saliva, are preferred.

The concentration of estriol in the fluid assayed is correlated with a standard value to determine when labor is imminent. The standard is usually (1) a predetermined range of estriol concentrations for the same body fluid in normal pregnant humans in the general population, either at the corresponding time in the pregnancy or a specific time relative to normal termination of pregnancy, or (2) a previously measured estriol concentration of the same body fluid of the same pregnant human. A measured higher concentration of estriol relative to the standard value is an indication of potential onset of pre-term labor. The method of the invention does not require the measurement of any other substance, such as the progesterone concentration in the body fluid, or require the measurement of total estriol production over a time interval. However, measurements of total estriol over a given time period, such as 24 hours, can be used with urine, if desired.

The first general standard set out above, namely a predetermined range of estriol concentrations for the same body fluid in normal pregnant humans in general, is typically obtained by using the same assay technique that will be used in the application of the method to an individual being tested, in order to ensure the highest correlation. Sufficient measurements are made in a normal population of pregnant women to produce a statistically significant range of normal values for the value to which a comparison will be made, which typically is at preselected time intervals during normal pregnancy. While comparison to a time immediately prior to normal delivery (38 to 40 weeks) is often used, other time periods can be used. For example, estriol levels during a given week of a individual pregnancy (i.e., that of the subject patient) can be compared to the normal range of concentrations for the same time period (e.g., the 20th week). Generally, the minimum concentration indicative of possible onset of labor is considered to be at least 1, preferably at least 2, more preferably at least 3, and most preferably at least 4, standard deviations above the mean estriol concentration determined just prior to the onset of labor for normal pregnant humans for any given body fluid.

It will be recognized by those familiar with statistics that the number of standard deviations used as an indication of pregnancy complications will be selected with an appropriate diagnosis goal in mind. For example, one standard deviation would encompass about 68% of normal samples; that is, 32% of normal samples would be expected to fall outside the lower and upper limits set by one standard deviation from the mean (16% would thus be expected to be above the selection limit). Thus, one standard deviation above the normal mean is not used for routine analysis, as it would include too many false positives. However, one standard deviation is appropriate for an assay that is desired to sweep in for further evaluation all possible candidates who might be predisposed toward pre-term labor, or this limit can be selected for patients known to have normal or low estriol values and relatively little variation between samples. One standard deviation can also be selected for a patient known to have problems with pre-term labor in order to determine when to more closely monitor the patient under controlled conditions (such as by having a patient admitted to a hospital for constant monitoring). Two standard deviations from the mean would encompass about 95% of normal samples; three standard deviations, about 99%; four standard deviations, more than 99%. These levels are more appropriate generally, especially for patients whose levels of estriol are known to be normal or slightly above normal or to vary from sample to sample as well as for assays with a high coefficient of variance.

It is not necessary to express the lower limit of the indication of labor (upper limit of the normal range) in standard deviations. Any other system that can be used to provide a statistically significant indication of probable onset of labor can be used. For example, the limit can be set to be a concentration that is at least as high as the 95th percentile concentration for normal patients for the same body fluid for a normal pregnancy. In any case, it is preferred to select a normal from the 38–42 week period for normal pregnancies, preferably at 40 weeks, and to monitor the concentration at 30 weeks or earlier.

Because of the many different possible clinical goals, the actual estriol level indicative of probable onset of pre-term labor is best selected by the attending physician after collecting data from several samples during the initial portion of the pregnancy and taking into consideration the time at which the measurement is being made. For example, in a normal pregnancy at week 30, the change expected in the estriol concentration prior to the onset of labor is smaller than 2 standard deviations from the mean concentration of estriol at 30 weeks. Thus, while assays in the first portion of a pregnancy (prior to 30 weeks) might use 3 or 4 standard deviations as an indication of onset of labor, two, one and a half, or even one standard deviation would be more appropriate in the later portion of a pregnancy (e.g., after 30 weeks) depending on the condition of the patient, other clinical indications in the mother known to the attending physician, and the health of the fetus. Of course, it is the earlier stages of a pregnancy that require greater attention to avoiding pre-term labor, because of the lack of fetal development at these stages and the high risk of infant death post partum. Pre-term labor is thus preferably considered to be any labor prior to the end of a normal 40-week term of pregnancy. The method of the invention is preferably used for pregnancies during weeks 20 to 36, when prolonging pregnancy for even a short time is most efficacious in reducing the effects of premature birth. However, the assay, particularly when used to detect rate of increase, is still applicable for pregnancies terminated by labor and delivery after the end of 40 weeks, and measurements made during this time period are also considered to fall within the scope of the invention. When applied to weeks 38 and higher, the invention is normally practiced using the "self-comparison" method discussed in more detail below; i.e., by comparing the measurement at a given time with a measurement made earlier with the same patient.

In a similar manner, subject to the same constraints discussed above, an assay concentration of at least 1, preferably at least 2, more preferably at least 3, and most preferably at least 4, standard deviations above the mean normal concentration for the same stage of pregnancy can also be used as an indication of an abnormal pregnancy and thus as an indication of possible onset of labor, although the probability is lower if the measured level does not reach the levels considered normal for weeks 38–42.

Standard values will vary with the specific body fluid whose concentration is being measured and with the specific assay being used (although to a lesser extent). Typical minimum indicative levels of labor onset in an assay that measures unconjugated estriol are as follows for the indicated body fluids (all concentrations are in nM): saliva, at least 3, preferably at least 5, more preferably at least 7; serum, 30, preferably at least 35, more preferably at least 45.

As an alternative to comparing estriol concentrations to those present in a normal population, a previously measured estriol concentration of the same body fluid of the same pregnant human can be used as a standard for comparison. In this case, what is being determined is usually the rate of increase in estriol concentration in the fluid being tested. A positive assay (i.e., indication of imminent onset of labor) is considered to be present when the measured concentration exceeds a previously measured estriol concentration made in the same body fluid in the same pregnant human female by 50%, preferably 75%, more preferably 100%, within one week. Again the selection of a particular rate of increase to label as the lower limit of labor onset is best selected by the attending physician for the particular reason desired. For example a screening test that is intended to collect potential problem patients into the hospital for further observation and study could select the 50% increase as its limit in order to avoid false negative results, while accepting the problems caused by including a relatively large number of false positives. Higher percentage increases as the minimum positive indication are more acceptable for home assays and the like, in the same manner as described above for standard deviations from the normal population mean. Increases in estriol concentration that meet the standards of this paragraph and additionally reach levels previously indicated to be indicative of the onset of labor in normal populations of patients are particularly likely to indicate imminent onset of labor.

It will be recognized by those skilled in clinical analysis that assays for a given analyte, including this assay for estriol, are not expected to be obtained or to be interpreted by an attending physician in the absence of additional information. Additionally, the results of any assay are best considered to be indicative of the probability of the presence of a clinical condition rather than as absolute proof. The same situation exists for the present invention. Nevertheless, an indication of increased probability of onset of labor is clinically useful information and can be used by a skilled medical practitioner in combination with other information to care for patients in a more informed manner than would be possible if the information were not available.

A preferred assay for use with the present invention is described in U.S. application Ser. No. 07/857,606, filed Apr. 1, 1992, which is herein incorporated by reference. This assay utilizes an enzyme-labelled component (here a labelled estriol molecule or derivative thereof) in a competitive binding assay for estriol. The assay is a non-instrumented enzyme immunoassay that provides present/not-present or "threshold" (+/−) analysis results at a preselected cut-off value and thus is well adapted for use with the present invention.

In a typical assay using this technique, the enzyme-labelled, competitive binding component comprises estriol (or the portion thereof used to generate the antibody used in the assay) bound to the immunogen that is used to produce the antibody of the assay. An enzyme label is bound to this moiety, preferably through a bulky linker such as an avidin-biotin complex. The use of such a competitive binding compound allows antibodies to be used without attempting to manipulate affinity of binding of antibody to competitor while still providing the steep competitive binding curve required for a +/− analysis.

In a typical such assay, antibody is attached to a solid surface, such as a microtiter plate well, a test tube, or a porous reagent strip (such as cellulose or glass fibers). The antibody-coated solid surface is then contacted simultaneously with a sample and with a competitive binding compound. By providing fewer antibody binding sites than are present in the combined total of analyte and competitive binding compound, only a fraction of the molecules in solution will bind to the solid surface. If there are no analyte molecules present, all of the binding sites will be taken up by the competitive binding compounds so that a maximum amount of enzyme is attached to the solid surface. When a substrate for the enzyme is contacted with the solid surface after the sample is washed away, reaction of the enzyme with the substrate provides a detectable signal (usually formation of a color) that indicates to the user the absence of analyte in the sample (a negative result). If analyte is present in the sample, analyte competes for binding sites so that less of the enzyme-labelled competitor can bind. By using a bulky binding composition, which binds less rapidly to the antibody than does the analyte, and by properly selecting the number of binding sites relative to the amount of sample added (which is a standard technique to one of skill in the art), analyte present at a concentration above a preselected minimum level will exclude binding of the competitive binding composition and thus binding of the enzyme to the solid substrate. An example of such a selection process to provide different threshold levels is set out in the cited patent application for estradiol. The same selection process can be used with estriol to carry out an assay of the invention. Thus, if sufficient analyte is present in the sample, after reaction no enzyme is present to produce a color change and the reaction mixture stays the same (thus a positive reaction using this reaction scheme).

Other reaction schemes can be used in which the formation of color is indicative of the presence of the analyte. The previous example is merely one of many types of competitive binding assays in which estriol can be measured.

Antibody production for use in an assay for estradiol is conventional and is not described here in detail. Techniques for producing antibodies are well known in the literature and are exemplified by the publication *Antibodies: A Laboratory Manual* (1988) eds. Harlow and Lane, Cold Spring Harbor Laboratories Press, and U.S. Pat. Nos. 4,381,292, 4,451,570, and 4,618,577. For an example of production of antibodies specific for estradiol, see Lasley et al., Fertility and Sterility (1985) 43:861–867, and Munro et at., Abstract, Society for Gynecologic Investigation, San Diego, March 1989. The same techniques can be used to produce antibodies to estriol. A brief discussion of general techniques for the production of antibodies specific for steroids is included for those who may be unfamiliar with the process.

An animal is injected with a composition containing estriol covalently attached to an immunogen, usually a protein, prepared as described above. Multiple injections or the use of an adjuvant will ensure maximum stimulation of the immune system and production of antibodies. If polyclonal antibodies are desired, they can be prepared by simply collecting blood from the immunized animal and separating the antibodies from other blood components by standard techniques. To obtain monoclonal antibodies, the spleen or lymphocytes from the immunized animal are removed and immortalized or used to prepare hybridomas by cell-fusion methods known to those skilled in the art. Antibodies secreted by the immortalized cells are screened to determine the clones that secrete antibodies of the desired specificity. For monoclonal anti-estriol antibodies, the antibodies must bind to estriol. Cells producing antibodies of the desired specificity are selected, cloned, and grown to produce the desired monoclonal antibodies.

Antibody can be attached to a solid surface for use in an assay of the invention using known techniques for attaching protein material to solid support materials. The solid support can include plastic surfaces of test tubes or microtiter plates, polymeric beads, dip sticks, or filter materials. The attachment methods include non-specific adsorption of the protein to the support and covalent attachment of the protein, typically through a free amino group, to a chemically reactive group on the solid support, such as an activated carboxyl, hydroxyl, or aldehyde group.

By detecting the probable onset of premature labor as described herein, a physician will be able to use existing techniques for delaying labor to avoid premature delivery and the resulting high risk of infant death.

The invention now being fully described, it will be apparent to one of ordinary skill in the art that many changes and modifications can be made thereto without departing from the spirit or scope of the appended claims.

All publications and patent applications mentioned in this specification are herein incorporated by reference to the same extent as if each individual publication or patent application was specifically and individually indicated to be incorporated by reference.

What is claimed is:

1. A method of screening for the potential onset of preterm labor in a pregnant human at 36 weeks gestation or earlier, which comprises:

(a) analyzing a sample body fluid from said pregnant human to determine unconjugated estriol concentration in the body fluid;

(b) correlating said concentration determined in step (a) with (1) a predetermined standard unconjugated estriol concentration for said body fluid, or (2) a previously measured unconjugated estriol concentration in said body fluid of said pregnant human to determine a rate of increase in unconjugated estriol concentration in the body fluid of said pregnant human; and (c) relating a higher concentration of unconjugated estriol in the body fluid of said pregnant human relative to said predetermined standard unconjugated estriol concentration, or relating an elevated rate of increase in unconjugated estriol concentration in the body fluid of said pregnant human as an indication of potential onset of pro-term labor in said pregnant human, wherein said relating does not consider progesterone concentration in said body fluid.

2. The method of claim 1, wherein said body fluid is saliva, plasma, serum, urine, cervical secretion, vaginal secretion, or sweat.

3. The method of claim 2, wherein said body fluid is saliva and said predetermined standard unconjugated estriol concentration is at least 5 nM.

4. The method of claim 2, wherein said body fluid is saliva and said predetermined standard unconjugated estriol concentration is at least 7 nM.

5. The method of claim 1, wherein said concentration determined in step (a) is determined at 30 weeks gestation or earlier and said predetermined standard unconjugated estriol concentration is at least as high as the 95th percentile concentration of unconjugated estriol for said body fluid for a normal pregnancy at 40 weeks gestation.

6. The method of claim 1, wherein said concentration determined in step (a) is determined within one week of the previously measured unconjugated estriol concentration in said body fluid of said pregnant human, and wherein an elevated rate of increase in unconjugated estriol concentration in the body fluid of said pregnant human is indicated when said concentration determined in step (a) exceeds the previously measured unconjugated estriol concentration in said body fluid of said pregnant human by at least 50%.

7. The method of claim 1, wherein said analyzing comprises a non-instrumented enzyme immunoassay for unconjugated estriol.

8. The method of claim 7, wherein said assay produces a color change at a concentration above said predetermined standard unconjugated estriol concentration.

9. A method of screening for the potential onset of preterm labor in a pregnant human at 36 weeks gestation or earlier, which comprises:

(a) analyzing a saliva sample from said pregnant human to determine the estriol concentration in said saliva sample;

(b) correlating said concentration determined in step (a) with (1) a predetermined standard estriol concentration for saliva, or (2) a previously measured estriol concentration in saliva of said pregnant human to determine a rate of increase in estriol concentration in saliva of said pregnant human; and (c) relating a higher concentration of estriol in the saliva sample of said pregnant human relative to said predetermined standard estriol concentration, or relating an elevated rate of increase in estriol concentration in the saliva of said pregnant human, as an indication of potential onset of pre-term labor in said pregnant human, wherein said relating does not consider progesterone concentration in said saliva.

* * * * *

UNITED STATES PATENT AND TRADEMARK OFFICE
CERTIFICATE OF CORRECTION

Patent No.: 5,480,776

Dated: Jan 2, 1996

Inventor(s): Vivian K. Dullien

It is certified that error appears in the above-identified patent and that said Letters Patent is hereby corrected as shown below:

In column 2, line 45, of the patent, delete "label, Similar" and replace with --label. Similar--.
Column 8, line 12:
In claim 1, line 22, delete "pro-term" and replace with --pre-term--.

Signed and Sealed this

Twenty-first Day of May, 1996

Attest:

BRUCE LEHMAN

*Attesting Officer*  *Commissioner of Patents and Trademarks*